United States Patent [19]

Boray

[11] 4,436,737
[45] Mar. 13, 1984

[54] ANTHELMINTIC COMPOSITIONS

[75] Inventor: Joseph C. Boray, Neutral Bay, Australia

[73] Assignee: Ciba-Geigy Corporation, Ardsley, N.Y.

[21] Appl. No.: 358,986

[22] Filed: Mar. 17, 1982

[30] Foreign Application Priority Data

Mar. 18, 1981 [CH] Switzerland ............... 1841/81

[51] Int. Cl.³ .................. A61K 31/66; A61K 31/415
[52] U.S. Cl. ............................. 424/225; 424/273 B
[58] Field of Search ........................ 424/225, 273 B

[56] References Cited

U.S. PATENT DOCUMENTS

| 4,159,337 | 6/1979 | Rowland | 424/273 B |
| 4,166,858 | 9/1979 | Rowland | 424/273 B |

FOREIGN PATENT DOCUMENTS

| 7117766 | 6/1972 | Netherlands | 424/225 |
| 601329 | 7/1978 | Switzerland | 424/225 |

OTHER PUBLICATIONS

Theorides et al., *Am. J. Vet. Res.*, vol. 37, pp. 1515–1516, (1976).
Crowley, Jr., et al., *Am. J. Vet. Res.*, vol. 37, pp. 1285–1286, (1976).

Primary Examiner—Jerome D. Goldberg
Assistant Examiner—Freda L. Abramson
Attorney, Agent, or Firm—Frederick H. Rabin; Bruce M. Collins

[57] ABSTRACT

The invention relates to a composition for the control of helminths in animals which contains a synergistic active ingredient combination which comprises the individual compounds of the formula I

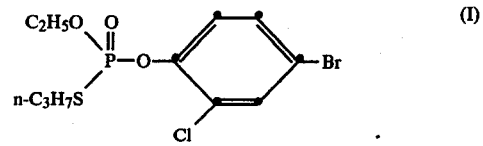

and of the formula II

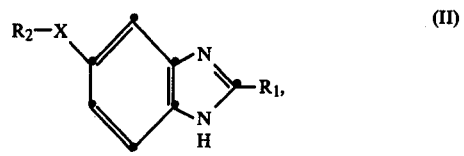

wherein $R_1$ is the —NH—COO—$R_3$ group, in which $R_3$ is an alkyl radical of 1 to 4 carbon atoms, preferably methyl, $R_2$ is an alkyl radical of 1 to 4 carbon atoms, preferably n-propyl, phenyl or phenyl substituted by halogen or alkyl, preferably unsubstituted phenyl, and X is —O—, —S— or —SO—, including the acid addition salts of the compounds falling under the formula II.

These synergistic compositions are used for controlling helminths, especially nematodes, in animals. The active ingredient combinations can be administered to the animals both as additive to ready prepared solid and liquid feeds and in the form of compositions, together with conventional carriers in solid or liquid form, orally, by injection, or by the pour-on method.

6 Claims, No Drawings

ANTHELMINTIC COMPOSITIONS

The present invention relates to novel anthelmintic compositions which contain an active ingredient combination, and to the use thereof for controlling helminths, especially nematodes, in animals.

The combination of active ingredients contained in the compositions of this invention has a synergistic effect which significantly exceeds the additive effect of the individual compounds. The active ingredient combination comprises the individual compounds of the formulae

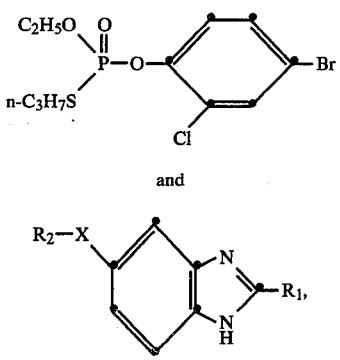

wherein $R_1$ is the —NH—COO—$R_3$ group, in which $R_3$ is an alkyl radical of 1 to 4 carbon atoms, preferably methyl, $R_2$ is an alkyl radical of 1 to 4 carbon atoms, preferably n-propyl, phenyl or phenyl substituted by halogen or alkyl, preferably unsubstituted phenyl, and X is —O—, —S— or —SO—, including the acid addition salts of the compounds falling under the formula II.

The compounds described above as active ingredients of the compositions of this invention are individually known to have anthelmintic properties. Compounds of the formula I are disclosed e.g. in Swiss Pat. No. 601 329, and those of the formula II are described in Am. J. Vet. Res. 37, 1285–86 and 1515–16 (1976), in Ann. Med. Vet. 120, 515–19 (1976), in Vet. Rec. 99, 267–70 (1976) and 101, 260–63 (1977) and in Belgian Pat. No. 793 358.

Combining different chemical compounds to produce a synergistic potentiation of action in pest control is gaining increasing importance as a result of the possibility thereby afforded of effectively counteracting the ever more frequently occurring resistance of parasites to individual compounds. An increase in the amount of the compounds employed, necessitated by the resistance developed by the pests, can thus substantially be avoided. The resultant saving in pesticides leads as a consequence both to economic as well as significant environmental advantages on account of the reduction in environmental impact. As regards the administration of anthelmintics to productive livestock, this saving can mean a lowering of the dose, which is simultaneously allied to a reduction in toxicity, so that the performance of the productive livestock is not impaired during therapy.

Helminthiasis in domestic animals and productive livestock is widespread and often results in growth inhibition and reduced performance of the infested animals. Extremely severe helminth infestation may even result in the death of the animals affected by it. Damage caused by helminth infestation assumes substantial dimensions in particular whenever herds of cattle fall victim to epidemic attack. The control and prevention of helminth infestation in productive livestock are therefore of the utmost importance in order to avoid damage, especially economic damage, in livestock production. A particular problem in this regard is the increasing resistance being developed by parasitic helminths to conventional individual anthelmintic compounds. In this connection, particular mention is to be made of the widespread nematodes, *Haemonchus contortus* and *Trichostrongylus colubriformis,* which occur mainly in sheep and which are already largely resistant to anthelmintics such as the frequently employed benzimidazole derivatives. In addition, combinations of individual compounds for controlling helminths in animals have already been proposed. However, these combinations have so far proved insufficiently effective to prevent the infestation of animals by parasitic helminths and the damage and losses in animal husbandry caused thereby.

It has now been found that the active ingredient combinations contained in the compositions of this invention and consisting of the compound of the formula I and a compound of the formula II, have a pronounced anthelmintic action with a broad activity spectrum against helminths which are parasites of animals, such as nematodes, cestodes and trematodes. Moreover, it has been found that the compositions of this invention are effective in particular against nematodes in sheep and cattle. This action is particularly pronounced in the control of nematodes of the species *Haemonchus contortus* and *Trichostrongylus colubriformis* in sheep.

The intrinsic advantage of the compositions of the present invention is to be seen in their property of being very effective also against resistant helminths.

With respect to the use of the compositions of the present invention, it is particularly advantageous that the active ingredient combinations contained therein are totally effective against the helminths to be controlled even at low rates of concentration. Toxic side-effects which may accompany high therapeutic doses are thus avoided, so that development and performance of the treated animals during therapy are scarcely impaired.

The following active ingredient combinations are preferred for controlling helminth infestation in animals:

(A) O-(4-bromo-2-chlorophenyl) O-ethyl S-propyl phosphorothioate (Profenofos) together with either (B) methyl 5-(n-propylthio)-1H-benzimidazol-2-ylcarbamate (Albendazole)

or (C) methyl 5-(phenylthio)-1H-benzimidazol-2-ylcarbamate (Fenbendazole)

or (D) methyl 5-(n-propoxy)-1H-benzimidazol-2-ylcarbamate (Oxibendazole)

or (E) methyl 5-(phenylsulfinyl)-1H-benzimidazol-2-ylcarbamate (Oxfendazole)

The preferred weight ratios of the compound of formula I to compounds of the formula II in the active ingredient combinations of the invention are in the range from 1:50 to 50:1. The ratio of 1:10 to 10:1 is advantageous for producing the synergistic effect. A ratio in the range from 1:5 to 5:1 has been found advantageous in particular for use against resistant helminths.

The synergistic effectiveness of the active ingredient combinations contained in the compositions of the invention is exemplified by means of the combinations in the following tests.

EXAMPLE 1

Test on sheep infested with benzimidazole-resistant *Haemonchus contortus* and *Trichostrongylus colubriformis*

1.1 Test substances

The test substances were administered to the test animals in the form of drench formulations.

Albendazole: Conventional commercial formulation containing 19 mg/ml of active ingredient (of formula B, page 4).

Compound of formula I: Drench formulation containing 25% active ingredient concentration.

Composition of the drench formulation 25.0 g of compound of the formula I
1.0 g of alkylaryl polyglycol ether (Emulgin 286)
0.2 g of tert-butyl hydroxyanisole and
104.6 g of di-n-butyl adipate (Cetiol B) = 100 ml.

1.2 Test procedure

1.2.1. Infection and therapy 27 sheep were each artificially infected with 5000 larvae (L₃) of *Haemonchus contortus* and with 12000 larvae (L₃) of *Trichostrongylus colubriformis*. The test sheep were divided into 5 groups of 4 animals and 1 group of 7 animals. 4 weeks after infection, the test substances (individual compounds or mixtures thereof) were administered intraruminally to the groups consisting of 4 animals. The group of 7 sheep received no medication and served as control.

1.2.2. Maintenance of the test animals

The test animals were kept in pens provided with concrete flooring and fed with feed consisting of 8 parts of wheaten hay, 1 part of linseed meal and 1% of mineral premix ad lib.

1.3 Evaluation

Samples of faecal matter were taken from the test animals rectally before, as well as 7, 14, 28 and 42 days after, medication, and the number of nematode eggs was determined using a standardised flotation method.

TABLE 1.4

| Active ingredient | Dose (mg/kg) | No. of eggs per g of faecal matter in individual test animals | | | | | Reduction in the number of eggs in faecal matter (%) |
|---|---|---|---|---|---|---|---|
| | | before treatment | 7 | 14 | 35 | 42 | |
| Albendazole | 2.3 | 8200 | 200 | 7800 | 8000 | 8200 | 0 |
| | | 5000 | 400 | 5300 | 11700 | 9300 | |
| | | 10900 | 2600 | 13700 | 9800 | 10100 | |
| | | 4100 | 200 | 15200 | 3700 | 3100 | |
| | | average 7050 | | | | average 7675 | |
| Albendazole | 4.6 | 4300 | 300 | 2700 | 1300 | 500 | 0 |
| | | 4600 | 400 | 900 | 2400 | 1400 | |
| | | 8300 | 800 | 4500 | 4100 | 1500 | |
| | | 14400 | 2200 | 17700 | 30500 | 37600 | |
| | | average 7900 | | | | average 10250 | |
| compound of the formula I | 10.0 | 3600 | 1400 | 4700 | 3600 | 4000 | 8.8 |
| | | 2600 | 1200 | 2100 | 1400 | 5800 | |
| | | 5300 | 900 | 1200 | 1700 | 700 | |
| | | 1000 | 300 | 600 | 400 | 900 | |
| | | average 3125 | | | | average 2850 | |
| Albendazole | 2.3 | 2000 | 0 | 0 | 100 | 100 | 93.6 |
| compound of the formula I | 10.0 | 1900 | 0 | 0 | 0 | 100 | |
| | | 700 | 0 | 0 | 0 | 0 | |
| | | 3200 | 0 | 0 | 200 | 300 | |
| | | average 1950 | | | | average 125 | |
| Albendazole | 4.6 | 2200 | 0 | 0 | 0 | 0 | 97.6 |
| compound of the formula I | 10.0 | 1900 | 0 | 0 | 0 | 0 | |
| | | 3500 | 0 | 0 | 0 | 0 | |
| | | 800 | 0 | 0 | 0 | 200 | |
| | | average 2100 | | | | average 50 | |
| Control | — | 3700 | 7100 | 10900 | 15200 | 9800 | — |
| | | 10400 | 11300 | 11100 | 5500 | 5300 | |
| | | 9300 | 12500 | 12800 | 10200 | 6600 | |
| | | 1800 | 4000 | 5300 | 3700 | 1800 | |
| | | 3800 | 4400 | 6800 | 4500 | 5000 | |
| | | 2400 | 4100 | 1900 | 4000 | 1900 | |
| | | 3500 | 5300 | 9800 | 18300 | 24300 | |
| | | average 4986 | | | | average 7814 | |

EXAMPLE 2

Test on sheep infested with benzimidazole-resistant *Haemonchus contortus* and *Trichostrongylus colubriformis*

2.1 Test substances

The test substances were administered to the test animals in the form of drench formulations.

Fenbendazole: Conventional commercial formulation containing 25 mg/ml of active ingredient (of formula C, page 4).

Compound of formula I: Drench formulation containing 12.5% active ingredient concentration.

Composition of the drench formulation 12.5 g of compound of the formula I
1.0 g of sorbitan trioleate (Span 85)
77.5 g of low viscosity paraffin oil
= 100 ml

2.2 Test procedure

2.2.1 Infection and therapy 30 sheep were each artificially infected with 5000 larvae (L₃) of *Haemonchus contortus* and with 12000 larvae (L₃) of *Trichostrongylus colubriformis*. The test sheep were divided into 6 groups of 4 animals and 1 group of 6 animals. 4 weeks after infection, the test substances (individual compounds or mixtures thereof) were administered intraruminally to the groups consisting of 4 animals. The group of 6 sheep received no medication and served as control.

2.2.2 Maintenance of the test animals

The test animals were kept in pens provided with concrete flooring and fed with feed consisting of 8 parts of wheaten hay, 1 part of linseed meal and 1% of mineral premix ad lib.

2.3 Evaluation

The test animals were sacrificed 14 to 16 days after medication and the adult nematodes were washed out of the infected stomach and intestinal sections and counted.

orally or in the form of solutions, emulsions, suspensions (drenches), powders, tablets, boluses or capsules. Conventional solid carriers are used for preparing these formulations, for example kaolin, talc, bentonite, common salt, calcium phosphate, cotton seed flour or liquids which do not react with the active ingredients, such as oils and other solvents and diluents which are harmless to the animal organism. Provided the physical and toxicological properties of solutions or emulsions permit it, the active ingredient combinations can also be administered to the animals by subcutaneous injection or by the pour-on method. Administration of the active ingredients to the animals by means of salt licks or molasses blocks is also possible.

The active ingredients or the mixtures containing them can also be added to the solid or liquid feeds. The ready-prepared feed contains the active ingredient combination preferably in a concentration of 0.005 to 0.1% by weight.

If the anthelmintic compositions are in the form of

TABLE 2.4

Results of the activity of the tested substances and mixtures thereof

| Active ingredients | Dose (mg/kg) | No. of nematodes in individual test animals 14–16 days after treatment | | Reduction in the number of helminths (%) | |
|---|---|---|---|---|---|
| | | *Haemonchus c.* | *Trichostrongylus c.* | H.c. | T.c. |
| Fenbendazole | 2.5 | 100 | 2613 | 63.7 | 0 |
| | | 475 | 2088 | | |
| | | 650 | 1763 | | |
| | | 350 | 2800 | | |
| | | average 395 | average 2316 | | |
| Fenbendazole | 5.0 | 500 | 3563 | 52.1 | 0 |
| | | 625 | 2325 | | |
| | | 650 | 2500 | | |
| | | 300 | 1838 | | |
| | | average 518 | average 2556 | | |
| Compound of the formula I | 10.0 | 0 | 288 | 99.4 | 64.5 |
| | | 0 | 63 | | |
| | | 25 | 375 | | |
| | | 0 | 2100 | | |
| | | average 6 | average 706 | | |
| Fenbendazole Compound of the formula I | 2.5 10.0 | 0 | 63 | 100 | 90.1 |
| | | 0 | 88 | | |
| | | 0 | 438 | | |
| | | 0 | —* | | |
| | | average 0 | average 196 | | |
| Fenbendazole Compound of the formula I | 5.0 10.0 | 0 | 0 | 100 | 96.5 |
| | | 0 | 188 | | |
| | | 0 | 88 | | |
| | | 0 | 0 | | |
| | | average 0 | average 69 | | |
| Control | | 1575 | 2250 | — | — |
| | | 750 | 1788 | | |
| | | 500 | 1400 | | |
| | | 1150 | 1975 | | |
| | | 2000 | 2538 | | |
| | | 525 | 2000 | | |
| | | average 1083 | average 1991 | | |

*no evaluation possible, as test animal prematurely met with a mishap

No toxicity symptoms were found clinically in the test animals at the therapeutically effective doses of the active ingredient combination.

The active ingredient combinations of the present invention are used for controlling parasitic helminths in domestic animals and productive livestock, such as cattle, sheep, goats, cats and dogs. They can be administered to the animals in both individual and repeated doses. Depending on the species of animal, the individual doses are preferably administered in amounts between 0.5 and 100 mg/kg of body weight. A better action is often attained by protracted administration, or it is possible to manage with lower total doses. The compositions can be administered to the animals per-feed concentrates, then suitable carriers are for example hay, production feeds, cereal feeds or protein concentrates. In addition to the active compounds, such feeds can contain additives, vitamins, antibiotics, chemotherapeutical agents or other pesticides, chiefly bacteriostats, fungistats, coccidiostats or also hormone preparations, substances having anabolic action or other substances which promote growth, enhance the quality of the flesh of slaughter animals, or are otherwise beneficial to the organism. They can also be combined with other anthelmintic agents, whereby their activity spectrum is broadened and adapted to given circumstances.

The anthelmintic compositions of the present invention are prepared in a manner known per se by homogeneously mixing and grinding the active ingredient combination consisting of the compound of the formula I and a compound of the formula II with suitable carriers, with or without the addition of dispersants or solvents which are inert to the active ingredients.

The anthelmintic compositions of the present invention may be processed e.g. to the following formulations:

Solid formulations:

granules (coated granules, impregnated granules and homogeneous granules); water-dispersible active ingredient concentrates (wettable powders).

Liquid formulations:

solutions, pastes, emulsions (especially ready for use suspensions (drenches).

For dusts and wettable powders, the granular size of the carriers is advantageously up to about 0.1 mm and for granules 0.01–0.5 mm.

The concentration of active ingredient combination in the solid formulations is in the range from 0.5 to 80%, and in the liquid formulations in the range from 0.5 to 50%.

These mixtures can also contain additives which stabilise the active ingredient combinations and/or non-ionic, anionic and cationic substances which ensure, for example, an improved wettability (wetting agents) and dispersibility (dispersants).

EXAMPLE

Water-dispersible powder mixture 25 parts by weight of an active ingredient combination of a compound of the formula I and a compound of the formula II are mixed thoroughly in a mixer with 7.5 parts by weight of an absorbent carrier, e.g. silicic acid, and 59.4 parts by weight of a carrier, e.g. bolus alba or kaolin, and 0.5 part by weight of oleic acid and 5.3 parts by weight of octyl phenyl polyglycol ether, 2.3 parts by weight of stearyl benzimidazole derivatives.

This mixture is ground in a dowelled disc mill or air jet mill to a particle size of 5 to 15 μm. The so obtained wettable powder gives a good suspension in water.

What is claimed is:

1. An anthelmintic composition comprising an anthelminitically effective amount of a combination of (a) O-(4-bromo-2-chlorophenyl) O-ethyl S-propyl phosphorothioate and (b) at least one member selected from the group consisting of (i) a compound of the formula:

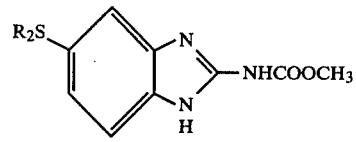

wherein $R_2$ is propyl or phenyl; and (ii) the acid addition salts thereof, wherein the weight ratio of (a) to (b) is from about 2:1 to about 4:1, in combination with a non-toxic carrier therefor.

2. A composition according to claim 1 wherein said combination comprises O-(4-bromo-2-chlorophenyl) O-ethyl S-propyl phosphorothioate and methyl-5-(n-propylthio)-1H-benzimidazol-2-ylcarbamate or an acid addition salt thereof.

3. A composition according to claim 1 wherein said combination comprises O-(4-bromo-2-chlorophenyl) O-ethyl S-propyl phosphorothioate and methyl-5-(n-phenylthio)-1H-benzimidazol-2-ylcarbamate or an acid addition salt thereof.

4. The method of combating helmintic infestation in animals which comprises orally administering thereto an effective amount of a composition according to claim 1.

5. A method according to claim 4 wherein said combination comprises O-(4-bromo-2-chlorophenyl) O-ethyl S-propyl phosphorothioate and methyl-5-(n-propylthio)-1H-benzimidazol-2-ylcarbamate or an acid addition salt thereof.

6. A method according to claim 4 wherein said combination comprises O-(4-bromo-2-chlorophenyl) O-ethyl S-propyl phosphorothioate and methyl-5-(n-phenylthio)-1H-benzimidazol-2-ylcarbamate or an acid addition salt thereof.

* * * * *